United States Patent [19]

Nelson et al.

[11] Patent Number: 4,701,485

[45] Date of Patent: Oct. 20, 1987

[54] MALONATE-BASED LIGHT STABILIZERS FOR PLASTICS

[75] Inventors: Richard V. Nelson, Wilmington, Del.; John F. Stephen, West Chester, Pa.

[73] Assignee: ICI Americas Inc., Wilmington, Del.

[21] Appl. No.: 893,616

[22] Filed: Aug. 6, 1986

Related U.S. Application Data

[63] Continuation-in-part of Ser. No. 786,800, Oct. 11, 1985, abandoned.

[51] Int. Cl.[4] .................... C07D 405/14; C08R 5/34
[52] U.S. Cl. ............................ 524/98; 524/102; 524/103; 540/543; 540/597; 546/15; 546/187
[58] Field of Search .................... 546/19, 187, 15; 524/103, 102, 98; 540/543, 597

[56] References Cited

U.S. PATENT DOCUMENTS 4,578,410 3/1986 Takahashi et al. ............... 546/187
4,621,110 11/1986 DiBattista ......................... 546/187

*Primary Examiner*—Robert T. Bond
*Attorney, Agent, or Firm*—Richard A. Rowe

[57] ABSTRACT

Malonate-derived acetal esters and amides possessing the polyalkyl piperidin-4-yl moiety are useful light stabilizers with synthetic polymer resins such as polyolefins and, in particular, polypropylene.

17 Claims, No Drawings

MALONATE-BASED LIGHT STABILIZERS FOR PLASTICS

This is a continuation-in-part of co-pending U.S. patent application Ser. No. 786,800, filed on Oct. 11, 1985, now abandoned.

The invention is directed to polymeric compositions which are resistant to degradation when exposed to actinic radiation. In particular, it is directed to resins such as polypropylene stabilized with effective amounts of cyclic acetals of aldehydes and ketones containing the polyalkyl piperidine moiety. The invention is further directed to a novel group of substances which are useful as additives for synthetic polymers which act to retard photo-degradation.

Many synthetic organic polymers deteriorate rapidly when exposed to sunlight. To circumvent this rapid degradation many additives have been developed to stabilize these resins against the harmful radiation. These additives include hydroxybenzophenones, hydroxybenzotriazoles, organonickel complexes, and a number of compounds which incorporate a hindered amine, such as 2,2,6,6-tetraalkylpiperidin, that is substituted in the 4-position. However, because none of these compounds sufficiently satisfy the stabilization requirements of polymers in their wide variety of forms and applications, there remains a need for new substances which are more satisfactory.

Stable synthetic polymer compositions of the invention are made by incorporation of an effective amount of the novel cyclic acetals. These acetals may be selected from those having the structures of formula I as shown in the Table of Structures which follows wherein:

$R^1$ is selected from hydrogen and an alkyl group of 1-5 carbon atoms such as methyl, ethyl, n-propyl, n-butyl, n-pentyl, especially hydrogen and methyl and most preferably hydrogen;

$R^2$ is selected from hydrogen, oxyl, hydroxyl, a straight or branched chain methylene-linked alkyl group having from 1 up to 18 carbon atoms such as methyl, ethyl, octyl, octadecyl, or 2-ethylhexyl, an alkanoyl group having 2-18 carbon atoms, such as acetyl, propanoyl, butanoyl, isopentanoyl, or stearoyl, an alkenyl group of 3-4 carbon atoms, an alkenoyl group having 3-6 carbon atoms, such as acryloyl, methacryloyl, crotonyl, an alkynyl group having 3 to 6 carbon atoms such as propargyl, or 2-butynyl, a cyanomethyl group, a 2,3-epoxypropyl group, an unsubstituted or substituted benzyl group of 7 to 15 carbon atoms such as 3,5-di-tert-butyl-4-hydroxybenzyl, 3-tert-butyl-4-hydroxy-benzyl or 3-tert-butyl-4-hydroxy-5-methyl benzyl, a group —CH$_2$CH(OR$^5$)—R$^6$ and a group of the formula

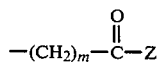

wherein Z is a group selected from —OR$^7$ and —N(R$^8$)(R$^9$) when m is 1 or 0 and when m is 0, Z can be a group —C(O)—OR$^{10}$, $R^5$ is selected from hydrogen, an aliphatic group of 1-18 carbon atoms such as those of $R^2$, an araliphatic group such as benzyl and phenethyl, and an aliphatic acyl group having 2-18 carbon atoms such as those of $R^2$, $R^6$ is selected from hydrogen, an alkyl group of 1-16 carbon atoms and phenyl, $R^7$ is selected from an alkyl group of 1-18 carbon atoms, a cycloalkyl of 5-12 carbon atoms such as cyclopentyl, cyclohexyl, cyclooctyl, cyclododecyl, allyl, benzyl, phenyl, and a group of formula II wherein $R^1$ and $R^2$ are as described above, and $R^8$ and $R^9$, same or different, are selected from hydrogen, an alkyl group having 1-8 carbon atoms such as methyl, ethyl, hexyl, a cycloalkyl group having 5-12 carbon atoms such as those of $R^7$, aryl groups having 6-10 carbon atoms such as 4-methylphenyl, 2-methylphenyl, 4-butylphenyl, and aralkyl groups having 7-15 carbon atoms such as benzyl, o,m,p-alkylsubstituted benzyl, and phenethyl. In addition, $R^8$ and $R^9$ together with the nitrogen atom to which they are attached can form a 5-7 membered ring such as pyrrolidine, piperidine and homopiperidine, and $R^{10}$ is selected from $C_{1-18}$ alkyl such as those of $R^2$, phenyl or benzyl, and is preferably $C_{1-2}$ alkyl.

$R^3$ and $R^4$ may independently be selected from hydrogen, an alkyl group of 1 to 14 carbon atoms such as methyl, ethyl, n-propyl, isopropyl, isooctyl, 3-heptyl, an alkenyl group of 2 to 4 carbon atoms, aryl, aralkyl, a group —(CH$_2$)$_n$CO—OR$^{11}$ where n is 0 or 1, and a group of formula III. $R^{11}$ is selected from a straight or branched chain alkyl group of up to 18 carbon atoms in length or a group of formula II.

When $R^3$ is hydrogen $R^4$ is a group of formula IV where A is a 1 to 4 carbon alkylene group, a phenylene group or a direct bond.

When $R^3$ is methyl $R^4$ can be a group of formula V where p is 1 or 2.

$R^3$ and $R^4$ together with the carbon atoms to which they are attached can form a cycloalkyl group having 5-12 carbon atoms such as cyclopentyl, cyclohexyl, cyclooctyl, cyclododecyl or denote a group of the formula VI or the group of formula VII where the carbon atom labelled 2 is the same as that labelled 2 in formula I.

X is either —O— or —NR$^{12}$— where $R^{12}$ is selected from hydrogen or an alkyl group of 1-8 carbon atoms such as methyl, ethyl, butyl, or octyl.

The acetals of formula I can be prepared from the corresponding aldehyde or ketone by reacting them with a diol of the formula (HOCH$_2$)$_2$C(CO$_2$R$^{13}$)$_2$ using a suitable acid catalyst and a suitable solvent as generally known in the art for the preparation of acetals. Examples of suitable acid catalysts are numerous, however, without introducing any limitations are mentioned p-toluenesulfonic acid and methanesulfonic acid. Examples of suitable solvents are cyclohexane and benzene. Although $R^{13}$ may be any alkyl group of 1 to 18 carbon atoms for this reaction it is preferred that $R^{13}$ be ethyl.

The preparation of the preferred diol has been described in the literature, i.e., Organic Synthesis Collective Vol. V, 381–383 (1973) and the material is commercially available. This procedure requires reacting a diethylmalonate with aqueous formaldehyde in the presence of a catalyst such as potassium bicarbonate and thereafter isolating the product by salting out and solvent extraction. The acetal resulting from reaction of diethyl bis(hydroxymethyl) malonate and the appropriate aldehyde or ketone is generally isolated by solvent extraction and after concentration can be purified by either distillation or crystalization.

Several of the dialkylester acetals serving as precursors for the compounds of this invention have been reported previously. In particular these compounds may be found in the works of M. Anteunis and C. Becu, Synthesis 1974, 23–25, S. Mager, et al., Studies Universities Babes-Bolyai, [SER] Chem. 1979, 24(1), 32–8 and S. Mager, et al., Monatsh. Chem. 1982, 113(5), 565–72.

These acetals are then transformed into the corresponding piperidine compounds of the invention in either a single step or in the cases where $R^2$ is other than hydrogen or alkyl an additional step is generally used. The transesterification or amidation reaction can be performed either neat or in a suitable solvent using basic catalysis as commonly used in the art. Examples of suitable catalysts without introducing any limitations are lithium amide and sodium methoxide. Examples of suitable solvents are ligroine and toluene.

The 4-hydroxypolyalkylpiperidines and the 4-aminopolyalkylpiperidines used to convert the acetals into the compounds of the invention are known from German Pat. No. 2,352,658 and U.S. Pat. No. 3,684,765. In general, the 4-hydroxy compounds are prepared from the corresponding 4-oxopiperidines by reduction via catalytic hydrogenation over Raney Nickel and the 4-amino compounds are synthesized via a reductive amination using ammonia or the particular primary amine of interest.

The 4-oxopiperidines of formula VIII can be prepared by reaction of ammonia with an aliphatic ketone. The reaction of ammonia with acetone to yield triacetoneamine is well-known and various processes exist in the art for its manufacture. The reacton of ammonia with methyl ethyl ketone has been described by W. Traube in Chem. Ber. 41,777 (1908).

Compounds of the formula VIII which carry other alkyl substituents in the 2-position and the 6-position can be prepared in a two step process following the procedures outlined in Helv. Chim. Acta 30,1114(1947) and Monatsh. Chem. 88,464(1957), followed by hydrolysis of the resulting pyrimidine.

The introduction of an alkyl, alkenyl, alkynyl, aralkyl and 2,3-epoxypropyl group can be achieved by reacton of the initially prepared ester or amide containing the free N—H of the polysubstituted piperidine with suitable halides like methyl iodide, ethyl bromide, propyl bromide, dodecyl chloride, and octadecyl chloride, allyl bromide, methallyl chloride, butenyl chloride, propargyl bromide, benzyl chloride, phenethyl bromide, and epichlorohydrin. The generated hydrogen halide can be scavenged by the addition of an inorganic base such as carbonate or hydroxide or by the addition of an organic amine such as triethylamine to the reaction mixture.

An alternative way of preparing the compounds of the invention which contain a 1-alkyl, 1-alkenyl, 1-alkynyl, 1-aralkyl, or 2,3-epoxypropyl group, especially when the desired invention compound is an ester, is to prepare the 1-substitutedpolyalkylpiperdin-4-ol as described in U.S. Pat. No. 4,014,887 and perform the transesterification in the manner as stated previously.

The introduction of an alkanoyl or an alkenoyl group can be performed by acylation of the parent N—H compound using the suitable acid halide or, when convenient, the acid anhydride. If the acid halide is used the generated hydrogen halide can be scavenged in the same manner as stated previously. Examples of such groups are acetyl chloride, propionyl chloride, hexanoyl chloride, dodecanoyl chloride, octadecanoyl chloride, acetic anhydride, and propionic anhydride.

For the compounds when $R^2$ is the group —$CH_2CH(OR^5)$—$R^6$ the substituent can be introduced by reaction of the parent N—H compound with the corresponding alkylene oxide such as ethylene oxide, propylene oxide and styrene oxide. The resulting hydroxy compound can be acylated in the manner commonly known in the art using the suitable acid halide and can be alkylated by generating the alkoxide using a base like sodium hydride and treating it with the desired alkyl or aralkyl halide.

When $R^2$ is the group —$CH_2$—$_mCOZ$ and m is zero the appropriate group can be attached by reacting the parent N—H compound with a chloroformate such as methyl chloroformate, ethyl chloroformate, allyl chloroformate, hexylchloroformate, decyl chloroformate, octadecyl chloroformate, and phenyl chloroformate. The preparation of the oxamide half esters can be achieved by reaction of the parent N—H compound with the oxalyl chloride monoalkylester such as oxalyl chloride monomethylester and oxalyl chloride monoethylester and scavenging the generated hydrogen chloride with a base as stated previously.

For preparation of the corresponding ureas the parent N—H compound can be treated with the suitable carbamyl halide such as methyl carbamyl chloride, ethyl carbamyl chloride, butyl carbamyl chloride, phenyl carbamyl chloride, dimethyl carbamyl chloride, diethylcarbarmyl chloride, dihexylcarbamyl chloride, pyrrolidine carbamyl chloride, piperidine carbamyl chloride, and homopiperidine carbamyl chloride. Alternatively, the ureas can be prepared by treating the parent N—H compound with the suitable isocyanate.

Compounds of formula I wherein $R^2$ is the oxyl radical are obtainable from the corresponding N—H compounds by oxidation with a peroxide such as hydrogen peroxide in the presence of a catalyst like sodium tungstate or with percarboxylic acids like metachloroperoxybenzoic acid.

When $R^2$ is the group —$(CH_2)_m$—$COZ$ and m is 1 the appropriate group can be attached by reacting the parent N—H compound with an ester of chloroacetic acid such as methyl chloroacetate, ethyl chloroacetate, cyclohexylchloroacetate, benzyl chloroacetate, allyl chloroacetate and phenyl chloroacetate.

The compounds of this invention are effective light stabilizers for synthetic organic polymers.

The following examples are offered to demonstrate but not limit the scope of the invention.

EXAMPLE 1

1,5-Dioxaspiro[5.5]undecane-3,3-dicarboxylic acid, diester with 2,2,6,6-tetramethylpiperidin-4-ol Preparation A. 1,5-Dioxaspiro[5.5]undecane-3,3-dicarboxylic acid, diethylester.

This substance is prepared according to the general procedure of Mager, et al., Stud. Univ. Babes-Bolyai Chem., 1979, 24(1), 32–38.

To a mixture of diethyl bis(hydroxymethyl) malonate (33.03 grams, 0.15 mol) and cyclohexanone (12.93 grams, 0.15 mol) in 150 ml of cyclohexane was added 0.75 grams p-toluenesulfonic acid. The reaction mixture was heated to reflux and the generated water was removed via a Dean-Stark trap. Upon completion of the ketalization (about 3–4 hours) the mixture was cooled to ambient temperature, washed with dilute aqueous sodium hydroxide and then water. After drying over the sodium sulfate and concentrating using a rotary evaporator, a viscous yellow-orange residue was obtained. Distillation yielded 38.1 g (bp 132°–142° C. at 0.10–0.15 mm) (78% of the above named compound).

A mixture of the compound of Preparation A (13.79 grams, 48 mmol) and 2,2,6,6-tetramethylpiperidin-4-ol (15.03 grams, 96 mol) in 100 milliliters of ligroin (90°–110° C.) was heated to reflux under a gentle stream of nitrogen. Lithium amide (120 mg) was added as catalyst. After 22 hours at reflux the reaction was diluted with additional hot ligroine, filtered to remove the insolubles and then cooled to allow crystallization. A white solid was obtained having a melting point of 161°–163° C., 17.5 grams, 70% yield). The structure of the above-named compound was supported by NMR and MS analysis.

Calculated for $C_{29}H_{50}N_2O_6$: C, 66.63%; H, 9.64%; N, 5.36%. Found: C, 66.93%; H, 9.65%; N, 5.35%.

EXAMPLE 2

1,5-Dioxaspiro[5.5]undecane-3,3-dicarboxylic acid, diester with 2,6-diethyl-2,3,6-trimethylpiperidin-4-ol This compound was prepared in a manner identical to the preparation of Example 1 with the substitution of 2,6-diethyl-2,3,6-trimethylpiperidin-4-ol for 2,2,6,6-tetramethylpiperidin-4-ol. The alcohol of this example was prepared by reduction of the corresponding ketone which was prepared as stated in U.S. Pat. No. 4,105,626, Column 12.

EXAMPLE 3

1,5-Dioxaspiro[5.5]undecane-3,3-dicarboxylic acid, diester with 1,2,2,6,6-pentamethylpiperidin-4-ol A mixture of 10.47 grams (36.3 millimole) of the compound prepared according to Preparation A and 12.44 g (72.6 millimole) of 1,2,2,6,6-pentamethylpiperidin-4-ol in 100 milliliters of ligroine (90°–110° C.) was heated to reflux under a general stream of nitrogen. 110 Milligrams of lithium amide was added as catalyst and the mixture was allowed to reflux for 18 hours. After this time the mixture was diluted with hot ligroine, filtered and partially concentrated. Crystallization yielded the product (9.8 grams, 49%) as a white solid having a melting point of 120°–122° C.

Calculated for $C_{31}H_{54}N_2O_6$: C, 67.60%; H, 9.88%; N, 5.09%. Found: C, 67.49%; H, 9.59%: N, 4.91%.

EXAMPLE 4

1,5,10,14-Tetraoxadispiro[5.2.5.2]hexadecane-3,3,12,12-tetracarboxylic acid, tetraester with 2,2,6,6-tetramethylpiperidin-4-ol Preparation B. 1,5,10,14-tetraoxaspiro [5.2.5.2]hexadecane-3,3,12,12-tetracarboxylic acid, tetraethylester.

This substance is prepared according to the general procedure of Mager et al., Monatsh Chem. 1982, 113(5), 565-572.

To a mixture of 1,4-cyclohexanedione (3.36 grams, 0.03 mol) and diethyl bis(hydroxymethyl)malonate (13.88 grams, 0.063 mol) in 300 milliliters of cyclohexane was added p-toluenesulfonic acid (0.27 grams). The mixture was heated to reflux and the produced water was removed by condensing in a Dean-Stark trap. After about 4 hours the mixture was cooled to ambient temperature and washed with aqueous sodium acetate. The addition of ethyl acetate was performed to help effect complete solubilization of the product which had crystallized. Drying over sodium sulfate and concentration yielded (14.52 grams, 94%) of the product as an off-white solid.

The product of preparation B (5.37 grams, 10.4 mmol) and 2,2,6,6-tetramethylpiperidin-4-ol (6.68 grams, 42.5 mmol) were combined in 100 milliliters of ligroine (90°–110° C.) and heated to reflux. Lithium amide (50 mg) was added as catalyst and a general stream of nitrogen was passed through the reaction flask. After 24 hours at reflux the mixture was diluted with hot ligroine and then cooled. The crystallized product was filtered and dried to give 6.91 grams (69%) of a white solid, mp 237°–240° C. (ethyl acetate).

Calculated for $C_{52}H_{88}N_4O_{12}$: C, 64.97%; H, 9.23%; N, 5.83%. Found: C, 64.39%; H, 9.35%; N, 5.58%.

EXAMPLE 5

1,5-Dioxaspiro[5.5]undecane-3,3-dicarboxylic acid, diester with 1-butyl-2,2,6,6-tetramethylpiperidin-4-ol A mixture of 5.2 g (10 mml) of the product of Example 1 was treated with 3.0 g (22 mmol) of 1-bromobutane in 25 ml of tetrahydrofuran containing triethylamine (22 mmol). The mixture was heated at reflux for 72 hours. After cooling and removal of the solvent the residue was partitioned between dichloromethane and water. The organic solution was dried (sodium sulfate) and concentrated. Purification of the residue yielded the desired product as evidenced by NMR and mass spectroscopies.

In the same manner as stated for the preparation of Example 5 the following are prepared:

(COMPOUND/ORGANIC HALIDE)

1,5-dioxaspiro[5.5]undecane-3,3-dicarboxylic acid, diester with 1-dodecyl-2,2,6,6-tetramethylpiperidin-4-ol/1-bromododecane 1,5-dioxaspiro[5.5]undecane-3,3-dicarboxylic acid, diester with 1-allyl-2,2,6,6-tetramethylpiperidin-4-ol/allyl bromide 1,5-dioxaspiro[5.5]undecane-3,3-dicarboxylic acid, diester with 1-propargyl-2,2,6,6-tetramethylpiperidin-4-ol/propargyl bromide 1,5-dioxaspiro[5.5]undecane-3,3-dicarboxylic acid, diester with 1-[2,3-epoxypropyl]-2,2,6,6-tetramethylpiperidin-4-ol/epichlorohydrin 1,5-dioxaspiro[5.5]undecane-3,3-dicarboxylic acid, diester with 1-ethoxycarbamylmethyl-2,2,6,6-tetramethylpiperidin-4-ol/ethyl chloroacetate 1,5-dioxaspiro[5.5]undecane-3,3-dicarboxylic acid, diester with 1-dodecyloxycarbamylmethyl-2,2,6,6-tetramethylpiperidin-4-ol/dodecyl chloroacetate 1,5-dioxaspiro[5.5]undecane-3,3-dicarboxylic acid, diester with 1-cyclohexyloxycarbamylmethyl-2,2,6,6-tetramethylpiperidin-4-ol/cyclohexyl chloroacetate 1,5-dioxaspiro[5.5]undecane-3,3-dicarboxylic acid, diester with 1-allyloxycarbamyl-2,2,6,6-tetramethylpiperidin-4-ol/allyl chloroformate 1,5-dioxaspiro[5.5]undecane-3,3-dicarboxylic acid, diester with 1-ethoxycarbamyl-2,2,6,6-tetramethylpiperidin-4-ol/ethyl chloroformate 1,5-dioxaspiro[5.5]undecane-3,3-dicarboxylic acid, diester with 1-phenyloxycarbamyl-2,2,6,6-tetramethylpiperidin-4-ol/phenyl chloroformate

EXAMPLE 6

2-[1-Methylethyl]-1,3-dioxacyclohexane-5,5-dicarboxylic acid, diester with 2,2,6,6-tetramethylpiperidin-4-ol Preparation C. 2-[1-methylethyl]-1,3-dioxocyclohexane-5,5-dicarboxylic acid, diethyl ester.

Diethyl bis(hydroxymethyl)malonate was reacted with isobutyraldehyde according to the procedure outlined for Preparation A.

(11.04 g, 40 mmol) of the material of Preparation C and 2,2,6,6-tetramethylpiperidin-4-ol (12.58 g, 80 mmol) in 100 ml of ligroine (90°–110° C.) was heated to reflux. To this solution was added (92 mg, 4 mmol) of lithium amide catalyst. The mixture was refluxed for 17 hours, diluted with 100 ml ligroine and the catalyst was neutralized with glacial acetic acid. The mixture was filtered hot and cooled. Crystallized product from ligroine weighed 8.53 g (42.6% yield) of a white powder m.p. 130°–132° C.

Calculated for $C_{27}H_{48}N_2O_6$: C, 65.29%; H, 9.74%; N, 5.64%. Found: C, 64.64%; H, 9.52%; N, 5.81%.

EXAMPLE 7

1,3-Bis[2,2'-[1,3-Dioxacyclohexane-5,5-dicarboxylic acid]]-propane, tetraester with 2,2,6,6-tetramethylpiperidin-4-ol Preparation D. Following the procedure outlined for Preparation A, 1 mol of glutaraldehyde was reacted with 2 mols of diethyl bis(hydroxymethyl)malonate to form 1,3-bis[2,2'-[1,3-dioxacyclohexane-5,5-dicarboxylic acid]]-propane, tetraethyl ester.

A mixture of 7.97 g (16 mmol) of Preparation D and 2,2,6,6-tetramethylpiperidin-4-ol (9.94 g, 63 mmol) in 100 ml of ligroine was heated to reflux. To this was added 46 mg. (2 mmol) of lithium amide as catalyst and refluxed for 17 hours. To this was added 100 milliliters of ligroine and enough glacial acetic acid to neutralize the catalyst. The solution was filtered hot and cooled to crystallize the product as (7.84 g, 52.3%) a white powder, m.p. 134°–135° C.

Calculated for $C_{51}H_{88}N_4O_{12}$: C, 64.53%; H, 9.34%; N, 5.90%. Found: C, 64.25%; H, 9.78%; N, 5.55%.

EXAMPLE 8

1,2-Bis[2,2'[2,-methyl-1,3-dioxacyclohexane-5,5-dicarboxylic acid]]-ethane, tetraester with 2,2,6,6-tetra methylpiperidin-4-ol Preparation E. 1,2-Bis[2,2'-[2-methyl-1,3-dioxacyclohexane-5,5-dicarboxylic acid]]-ethane, tetraethylester.

Diethyl bis(hydroxymethyl)malonate (2 equivs.) was reacted with 2,5-hexanedione according to the procedure outlined for Preparation A. The product was obtained as a beige solid.

A mixture of 5.38 g (10.38 mmol) of the compound of Preparation E and 6.60 g (42.56 mmol) of 2,2,6,6-tetramethylpiperidin-4-ol in 40 ml of ligroine was heated to reflux and 25 mg (1 mmol) of lithium amide was added. The mixture was stirred at reflux with the intermittent addition of fresh ligroine. After 7 hours the catalyst was destroyed by the addition of acetic acid and the mixture was filtered and permitted to crystallize. The product was isolated as a white powder (mp 143°–146° C.) and was characterized by NMR and mass spectroscopy.

EXAMPLE 9

1,5-Dioxaspiro[5.11]heptadecane-3,3-dicarboxylic acid, diester with 2,2,6,6-tetramethylpiperidin-4-ol Preparation F. 1,5-dioxaspiro[5.11]heptadecane-3,3-dicarboxylic acid, diethyl ester.

Diethyl bis(hydroxymethyl) malonate was reacted with cyclododecanone according to the procedure outlined for Preparation A. The product was obtained as a white solid (mp 58°–62° C.).

A mixture of 6.96 g (16.47 mmol, 91% purity—of the compound of Preparation F and 5.44 g (34.60 mmol)) of 2,2,6,6-tetramethyl-piperidin-4-ol in 100 ml of ligroine was heated to reflux and 50 mg (2 mmol) of lithium amide was added. The mixture was heated to reflux with solvent occasionally being removed and replenished. The mixture was heated for 20 hours before the catalyst was destroyed with acetic acid and the mixture was filtered and permitted to crystallize. The product was isolated as a white solid (mp 169°–171° C.) and was characterized by NMR and mass spectroscopy.

EXAMPLE 10

2-[3-Heptyl]-1,3-dioxacyclohexane-5,5-dicarboxylic acid, diester with 2,2,6,6-tetramethylpiperidin-4-ol Preparation G. 2-[3-heptyl]-1,3-dioxacyclohexane-5,5-dicarboxylic acid, diethyl ester.

Diethyl bis(hydroxymethyl)malonate was reacted with 2-ethylhexanal according to the procedure outline for Preparation A. The product was isolated as a colorless liquid (bp 125°–130° C. @0.20 mm).

A mixture of 5.98 g (18 mmol) of the compound of Preparation G and 5.69 g (36 mmol) of 2,2,6,6-tetramethylpiperidin-4-ol in 60 ml of ligroine was heated to reflux and then 23 mg. (1 mmol) of lithium amide was added. The ligroine was removed gradually and replaced as necessary. After 17 hours at reflux the solution was cooled, washed with water (3×100 ml), dried (sodium sulfate) and concentrated to yield a white powder. Recrystallization from ethanol/water yield the product (7.35 g, 74%) having a melting point of 79°–85° C. Characterization was completed by NMR and MS.

EXAMPLE 11

2-Vinyl-1,3-dioxacyclohexane-5,5-dicarboxylic acid, diester with 2,2,6,6-tetramethylpiperidin-4-ol Preparation H. 2-vinyl-1,3-dioxacyclohexane-5,5-dicarboxylic acid, diethyl ester.

Diethyl bis(hydroxymethyl)malonate was reacted with acrolein according to the procedure outlined for preparation A with the exception that trifluoroacetic acid was used as the acid catalyst. The product was a colorless liquid (bp 99°–102° C. @0.20 mm).

A mixture of 5.37 g (21 mmol) of Preparation H and 6.60 g (42 mmol) of 2,2,6,6-tetramethylpiperidin-4-ol, in 60 ml of ligroine was heated to reflux and then 23 mg (1 mmol) of lithium amide was added. The ligroine was removed gradually and replaced with fresh solvent. After 4.5 hours at reflux the catalyst was destroyed by the additon of glacial acetic acid and the hot solution was filtered. The product crystallized from this solution to yield a white powder (6.07 g, 61%) which had a melting point of 96°–98° C.

Calculated for: $C_{26}H_{44}N_2O_6$: C, 64.97%; H, 9.23%; N, 5.83%. Found: C, 64.97%; H, 8,78%; N, 5.56%.

EXAMPLE 12

1,5-Dioxaspiro[5.5]undecane-3,3-dicarboxylic acid, diester with 1-acetyl-2,2,6,6-tetramethyl piperidin-4-ol A mixture of the compound of Example 1 (17.23 g, 0.033 mol) and acetic anhydride (40.0 g, 0.39 mol) in 70 ml of chloroform was refluxed for 48 h. The pale yellow solution was cooled, diluted with additional chloroform and washed with saturated aqueous sodium carbonate solution (3×200 ml) and then with water (3×200 ml). The organic layer was dried over sodium sulfate and concentrated to yield a brown oil. Trituration with ether yielded a yellow-brown solid. Recrystallization from ethyl acetate gave a white powder (9.30 g, 46%) which had a melting point of 137°–138° C.

Calculated for $C_{33}H_{54}N_2O_8$: C, 65.32%; H, 8.97%; N, 4.62%. Found: C, 65.30%; H, 8.83%; N, 4.36%.

EXAMPLE 13

2-[1-Methylethyl]-1,3-dioxacyclohexane-5,5-dicarboxylic acid, diester with 1-acetyl-2,2,6,6-tetramethyl piperidin-4-ol To the product of Example 6 (20.0 g, 40 mmol) combined with 20 ml of chloroform was added acetic anhydride (32.7 g, 0.32 mol). The mixture was heated to reflux and maintained for 24 hours. The excess acetic anhydride was removed by distillation. The residue was dissolved in 100 ml of chloroform, washed with dilute aqueous sodium hydroxide and water. The organic solution was dried (sodium sulfate) and evaporated to yield a yellow liquid. Trituration with petroleum ether (35°–60° C.) yielded a white solid (17.55 g, 75%) having a melting point of 101°–102° C.

Calculated for: $C_{31}H_{52}N_2O_8$: C, 64.11%; H, 9.02%; N, 4.82%. Found: C, 64.66%; H, 9.07%; N, 4.89%.

EXAMPLE 14

1,5-Dioxaspiro[5.5]undecane-3,3-dicarboxylic acid, diester with 1-acryloyl-2,2,6,6-tetramethylpiperidin-4-ol To a solution of the product of Example 1 (5.23 g, 10 mmol) in 40 ml of tetrahydrofuran was added a solution of acryloyl chloride (2.0 g, 22 mmol) in 25 ml of tetrahydrofuran dropwise over a period of 20 minutes. Upon completion of the addition the mixture was permitted to stir at ambient temperature for 24 hours. The mixture was diluted with ether, neutralized with aqueous soduim hydroxide and partitioned with water. The organic solution was dried (magnesium sulfate) and concentrated to yield the crude product. Trituration with ether/petroleum ether (35°–60° C.) yielded the product as a white solid (mp 129°–132° C.). This material was characterized by NMR and mass spectroscopies.

In a manner identical to the procedure of Example 14 the following illustrative compounds can be prepared:
1,5-dioxaspiro[5.5]undecane-3,3-dicarboxylic acid, diester with 1-hexanoyl-2,2,6,6-tetramethylpiperidin-4-ol
1,5-dioxaspiro[5.5]undecane-3,3-dicarboxylic acid, diester with 1-stearoyl-2,2,6,6-tetramethylpiperidin-4-ol
1,5-dioxaspiro[5.5]undecane-3,3-dicarboxylic acid, diester with 1-dimethylcarbamyl-2,2,6,6-tetramethylpiperidin-4-ol
1,5-dioxaspiro[5.5]undecane-3,3-dicarboxylic acid, diester with 1-diethylcarbamyl-2,2,6,6-tetramethylpiperidin-4-ol

EXAMPLE 15

1,5-Dioxaspiro[5.5]undecane-3,3-dicarboxylic acid, diester with 1-butylcarbamyl-2,2,6,6-tetramethylpiperidin-4-ol To a solution of the product of Example 1 (5.23 parts) in 40 ml of tetrahydrofuran was added a soluton of butyl isocyanate (2.08 parts) in 20 parts of tetrahydrofuran. The mixture was allowed to stir at ambient temperature for 24 hours where upon concentration of the mixture and purificaton of the crude reaction mixture yielded the desired product as demonstrated by NMR and mass spectroscopies.

Similarly the following compounds are prepared:
1,5-dioxa[5.5]undecane-3,3-dicarboxylic acid, diester with 1-cyclohexylcarbamyl-2,2,6,6-tetramethylpiperidin-4-ol
1,5-dioxaspiro[5.5]undecane-3,3-dicarboxylic acid, diester with 1-allylcarbamyl-2,2,6,6-tetramethylpiperidin-4-ol

EXAMPLE 16

1,5-Dioxaspiro[5.5]undecane-3,3-dicarboxylic acid, diester with 1-[2-hydroxyethyl]-2,2,6,6-tetramethylpiperidin-4-ol To a mixture of the product of Example 1 (5.23 g, 10 mmol) in isopropanol was added ethylene oxide 44 g, 100 mmol). The mixture was charged in an autoclave and heated. Upon completion of the reaction the mixture was concentrated and purified by recrystallization to yield the desired product as indicated by NMR and mass spectroscopy.

Similarly can be prepared the products derived form propylene oxide and styrene oxide.

EXAMPLE 17

1,5-Dioxaspiro[5.5]undecane-3,3-dicarboxylic acid, diester with 1-[2-stearoyloxyethyl]-2,2,6,6-tetra methylpiperidin-4-ol The product of Example 16 (6.10 parts) was combined with stearoyl chloride (6.36 parts) and triethylamine (2.22 parts) in tetrahydrofuran. The mixture was stirred at ambient temperature for 18 hours before being partitioned between dichloromethane and water. The organic solution upon drying and concentration yielded the product as evidenced by NMR and mass spectroscopy.

EXAMPLE 18

1,5-Dioxaspiro[5.5]undecane-3,3-dicarboxylic acid, diester with 1-cyanomethyl-2,2,6,6-tetramethyl piperidin-4-ol A mixture of the product of Example 1 (5.23 parts) and acetone cyanohydrin (1.87 parts) and excess formaldehyde (37% aqueous) was heated at reflux for 18 hours. The mixture was cooled, basified and extracted with ether. The organic solution was dried (magnesium sulfate) and concentrated to yield the crude product. Purification yielded the desired product as evidenced by NMR and mass spectroscopy.

EXAMPLE 19

2,2-Dimethyl-1,3-dioxacyclohexane-5,5-dicarboxylic acid, diester with 2,2,6,6-tetramethylpiperidin-4-ol Preparation E.' 2,2-Dimethyl-1,3-dioxacyclohexane-5,5-dicarboxylic acid, diethyl ester is prepared according to the procedure of Preparation A by reacting stoichiometric amounts of acetone with diethyl bis(hydroxymethyl)malonate (bp 102-104° C @0.25mm).

The spiroacetal of Preparation E' (13.0 g, 50 mmol) and 2,2,6,6,-tetramethylpiperidin-4-ol (15.7 g, 100 mmol) in 100 milliliters of ligroine (90-110° C) at reflux for 16 hrs. in admixture with 120 mg lithium amide catalyst is thereafter neutralized with glacial acetic acid in 100 milliliters of ligroine. The mixture is filtered hot and cooled to precipitate product.

In a manner identical to Example 19 the preparation of the following compounds are prepared:

2-methyl-2-phenyl-1,3-dioxacyclohexane-5, 5-dicarboxylic acid, diester with 2,2,6,6-tetramethylpiperidin-4-ol 2-ethyl-2-methyl-1,3-dioxacyclohexane-5, 5-dicarboxylic acid, diester with 2,2,6,6-tetramethylpiperidin-4-ol 2-methyl-2-pentyl-1,3-dioxacyclohexane-5, 5-dicarboxylic acid, diester with 2,2,6,6-tetramethylpiperidin-4-ol 2,2-diethyl-1,3-dioxacyclohexane-5, 5-dicarboxylic acid, diester with 2,2,6,6-tetramethylpiperidin-4-ol 2-butyl-2-ethyl-1,3-dioxacyclohexane-5, 5-dicarboxylic acid, diester with 2,2,6,6-tetramethylpiperidin-4-ol 2,2-di-n-hexyl-1,3-dioxacyclohexane-5, 5-dicarboxylic acid, diester with 2,2,6,6-tetramethylpiperidin-4-ol 2,2-di-iso-butyl-1,3-dioxacyclohexane-5, 5-dicarboxylic acid, diester with 2,2,6,6-tetramethylpiperidin-4-ol

EXAMPLE 20

2-Ethoxycarbonylmethyl-2-methyl-1,3-dioxacyclohexane-5, 5-dicarboxylic acid, diester(triester) with 2,2,6,6-tetramethylpiperidin-4-ol Preparation I: 2-Ethoxycarbonylmethyl-2-methyl-1,3-dioxacyclohexane-5,5-dicarboxylic acid, diethyl ester was prepared according to the procedure of Preparation A. The product was obtained as a colorless liquid (bp 144-148° C. @0.15 mm).

A mixture of the compound of Preparation I (4.99 g, 15 mmol) and 2,2,6,6-tetramethylpiperidin- 4-ol (7.39g, 47 mmol) in 100 ml of ligroine was heated to reflux and lithium amide (55 mg) was added as catalyst. The mixture was maintained at reflux with intermittent removal of the solvent collected in the Dean-Stark trap and replacement with fresh solvent. After refluxing for 22hours the mixture was cooled, the catalyst was neutralized with acetic acid and the reaction mixture was partitioned with water. The organic solution was dried (sodium sulfate) and concentrated to yield the product mixture as a viscous, light orange liquid. The identity of the products was determined by NMR and mass spectroscopies.

In a manner identical to the preparation of Example 20 the compound derived from 2-ethoxycarbonyl-1,3-dioxacyclohexane-5,5-dicarboxylic acid, diethyl ester can be made.

EXAMPLE 21

2-[2-[3,5-Di-tert-butyl-4-hydroxphenyl]]ethyl-2-methyl-1,3-dioxacyclohexane-5,5-dicarboxylic acid, diester with 2,2,6,6,-tetramethylpiperidin-4-ol Preparation J: 2-[2-[3,5-Di-tert-butyl-4-hydroxyphenyl]]ethyl-2-methyl-1,3-dioxacyclohexane-5,5-dicarboxylic acid, diethyl ester Diethyl bis(hydroxymethyl) malonate was reacted with 1-[3,5-di-tert-butyl-4-hydroxyphenyl]-butan-3-one according to the procedure outlined for Preparation A. The product was obtained as a yellow, viscous liquid.

A mixture of 2.39 g (5.0 mmol) of the compound of Preparation I and 1.73 g (11.0 mmol) of 2,2,6,6-tetramethylpiperidin-4-ol in 20 ml of ligroine was heated to reflux and then 11 mg (0.5 mmol) of lithium amide was added. the mixture was permitted to stir for 18 hours at reflux, diluted with ligroine, filtered and permitted to crystallize. The product was obtained as a white solid (2.43 g, 70%) having a melting point of 123-126°C.

Calculated for: $C_{41}H_{68}N_2O_7$: C, 70.25%; H, 9.78%; N, 4.00% Found: C, 70.13%; H, 9.89%; N, 4.21%

EXAMPLE 22

1,5-Dioxaspiro[5.5]undecane-3,3-dicarboxylic acid, diamide with 4-amino-2,2,6,6-tetramethylpiperidine To a mixture of (5.23 parts) of the compound of Example 1 and (3.43 parts) of 4- amino-2,2,6,6-tetramethylpiperidine in 30 ml of DMSO was added sodium hydride (0.5 parts). The mixture was heated to 100° C and maintained for 12 hours. The crude reaction mixture was partitioned between ethyl acetate and water after cooling. The organic solution was dried (sodium sulfate) and concentrated. After subsequent purification the product was characterized by NMR and mass spectroscopy.

The spiroacetal derivatives of the invention are particularly useful as light stabilizers for synthetic polymers which undergo degradation in the presence of air and actinic radiation. As used herein polymers are intended to embrace polyolefins including homopolymers of olefins such as low density and high density polyethylene, polypropylene, polystyrene, polybutadiene, polyisoprene and the like; and copolymers of olefins with other ethylenically unsaturated monomers such as ethylene-propylene copolymer, ethylene-butylene copolymer, ethylene-vinyl acetate copolymer, styrene-butadiene copolymer, acrylonitrilestyrene-butadiene copolymer and the like; polyvinylchlorides and polyvinylidene chlorides including homopolymers of each of vinylchloride and vinylidene chloride, vinylchloride-vinylidene copolymers and copolymers of each vinylchloride and vinylidene chloride with vinyl acetate or other ethylenically unsaturated monomer; polyacetal as such polyoxymethylene and polyoxyethylene; polyesters such as polyethyleneterephthalate; polyamide such as 6-nylon, 6,6-nylon and 6,10-nylon and polyurethanes and polymers derived from α,β-unsaturated acids and derivatives thereof, polyacrylates and polymethacrylates, polyacrylic amides and polyacrylonitrile, as well as copolymers of acrylic acid and one or more of its derivatives with a melamine-formaldehyde resin.

Synthetic polymers have been widely utilized in the art in view of their excellent properties in various forms or shapes, for example, filaments, fibers, yarns, filament sheet, other molded articles and other molded articles made from latex and foam. However, these polymers have some drawbacks such as poor light and heat stabilities among others. Stated illustratively, polyolefins and polyurethane elastomers frequently tend to undergo severe deterioration when exposed to light such as sunlight or ultraviolet light and polyvinyl chloride and polyvinylidene chlorides frequently tend to deteriorate and become colored by the action of light and heat together with elimination of hydrogen chloride. Polyamides are also frequently subjected to photodegradation. For the purpose of stabilizing these synthetic polymers against such degradation, these have been proposed in the art a number of stabilizers. For example, in the case of polyolefins, benzotriazole and benzophenone compounds; for polyurethanes, phenol compounds and benzophenone compounds: and for polyvinylchlorides and vinylidene chlorides, lead salts such as basic lead silicate and trisilicate, lead maleate and organic tin compounds such as dibutyltinlaurate and dibutyltinmaleate.

The resin should have incorporated within an effective stabilizing amount of a compound described by formula I. The amount will depend upon the nature of the plastic and the amount of radiation to which the plastic will be subject. Generally an amount between about 0.01% and 5 0% by weight of the polymer is effective. Preferably they may be used in concentrations between 0.05 and 1% by weight.

In addition, the light stabilizers of formula I may be used with fillers and additional stabilizers including antioxidants, flame retardant stabilizers, anti-slipping and antistatic agents, supplemental light stabilizers, pigments, dyes, lubricants, etc.

Suitable antioxidants include those of the hindered phenol type such as 2,6-di-t-butyl-p-cresol; 4,4'-bis(2,6-di-t-butylphenol); 4,4'-bis(2,6-diisopropylphenol); 2,4,6-tri-t-butylphenol; 2,2'-thiobis (4-methyl-6-t-butylphenol); octadecyl-2(3',5'-di-t-butyl-4'-hydroxyphenyl)-propionate: pentaerythrityl tetrakis(3,5-di-t-butyl-4-hydroxyphenyl)propionate; 1,3,5-tris(3',5'-di-t-butyl-4-hydroxybenzyl) isocyanurate; 1,3,5-tris((3',5'-di-t-butyl-4'-hydroxyphenyl) propionate) isocyanurate; 1,3,5-tris(3 ,5'-di-t-butyl-4'-hydroxybenzyl)-2,4,6-dimethylbenzyl)-s-triazine-2, 4,6-(1H,3H,5H)-trione and esters of thiodipropionic acid such as dilaurylthiodipropionate and distearylthiodipropionate etc.; hydrocarbyl phosphites such as triphenyl phosphite, trinonyl phosphite, didodecyl pentaerythritol diphosphite, diphenyldecyl phosphite, tris-(2,4-di-t-butylphenyl)phosphite, bis(2,4-di-t-butylphenyl)pentaerythritol diphosphite, etc, in combinations thereof.

Suitable supplemental light stabilizers include those of the benzotriazole class, such as 2-(2 -hydroxy-5-t-octylphenyl)benzotriazole; 2,(2'-hydroxy-3',5'-di-t-butyl-phenyl)-5-chlorobenzotriazole; 2-(2'-hydroxy-5'-methylphenyl)benzotriazole; 2-(2'-hydroxy-3'-t-butyl-5'-methylphenyl)-5-chlorobenzotriazole; 2-(2'-hydroxy-5'-t-butylphenyl)benzotriazole; 2-(2'-hydroxy-3',5'-di-t-amylphenyl)-benzotriazole; those of the hydroxybenzophenone type such as 2-hydroxy-4-methoxybenzophenone; 2-hydroxy-4-octyloxybenzophenone; 2,2'-dihydroxy-4,4'-di-methoxybenzophenone; hindered phenol esters, such as n-hexadecyl-3,5-di-t-butyl-4-hydroxybenzoate, and 2',4'-di-t-butylphenol-3, 5-di-t-butyl-4-hydroxybenzoate; metal complexes such as nickel complexes of 2,2'-thiobis(4-6-octylphenol), nickel butylamine complexes of 2,2'-thiobis(4-t-octylphenol): nickel complexes of bis(4-t-octyl-phenol)sulphone; nickel dibutyl thiocarbamate; nickel salts of 4-hydroxy-3,5-di-t-butylbenzylphosphonic acid monoalkyl esters where alkyl is methyl, ethyl, propyl, butyl etc.; nickel complexes of to 2-hydroxy-4-methylphenyl undecylketoneoxime. Further illustrative examples of suitable antioxidants of supplemental light stabilizers can be found in columns 3 and 4 of U.S. Pat. Nos. 3,488,290 and 3,496,134.

EXAMPLES 23-28

In order to further illustrate the effectiveness of the above-described compounds as light stabilizers the previously described materials of Examples 1, 3, 4, 6, 7 and 12 were each incorporated into a commercially available polypropylene resin manufactured by Hercules Corporation as PRO-FAX[3] 6301 Polypropylene Resin. The light stabilizers were incorporated with the polypropylene by solvent blending (methylene chloride) at concentrations of 0.25% by weight of the total resin composition and as a primary antioxidant stearyl beta-3,5-di-t-butyl-4-hydroxyphenylpropionate was used at a concentration of 0.2%. The resin was then extruded at 200° C and compression molded at 6,000 psi at 188° C to produce films having thicknesses of 5 mils. A control film was produced by an identical procedure with the light stabilizer omitted. Each film was exposed to Xenon Arc in an Atlas Weather-o-meter until the infrared carbonyl absorption increased by 0.5, which is considered to be the failure point.

TABLE I

| Example No. | Stabilizer | Hours to Failure |
|---|---|---|
|  | Control | 300 |
| 23 | Product of Example 1 | 3760 |
| 24 | Product of Example 3 | 3930 |
| 25 | Product of Example 4 | 3780 |
| 26 | Product of Example 6 | >3000 |
| 27 | Product of Example 7 | >3000 |
| 28 | Product of Example 12 | 2280 |

Table of Structures

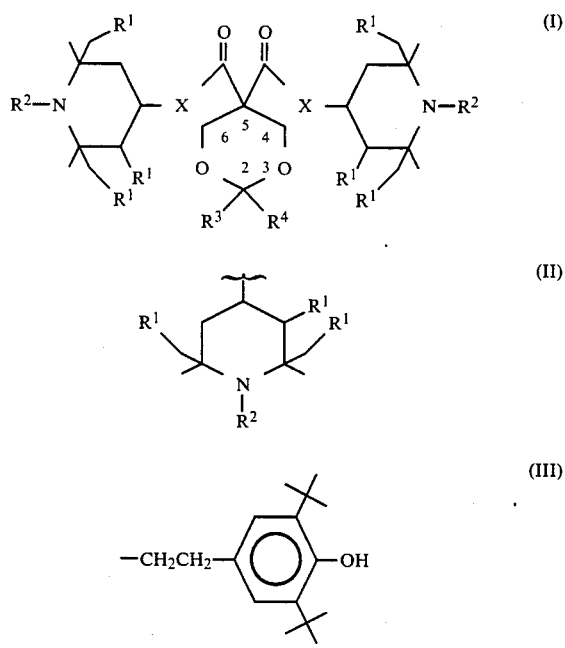

-continued
Table of Structures

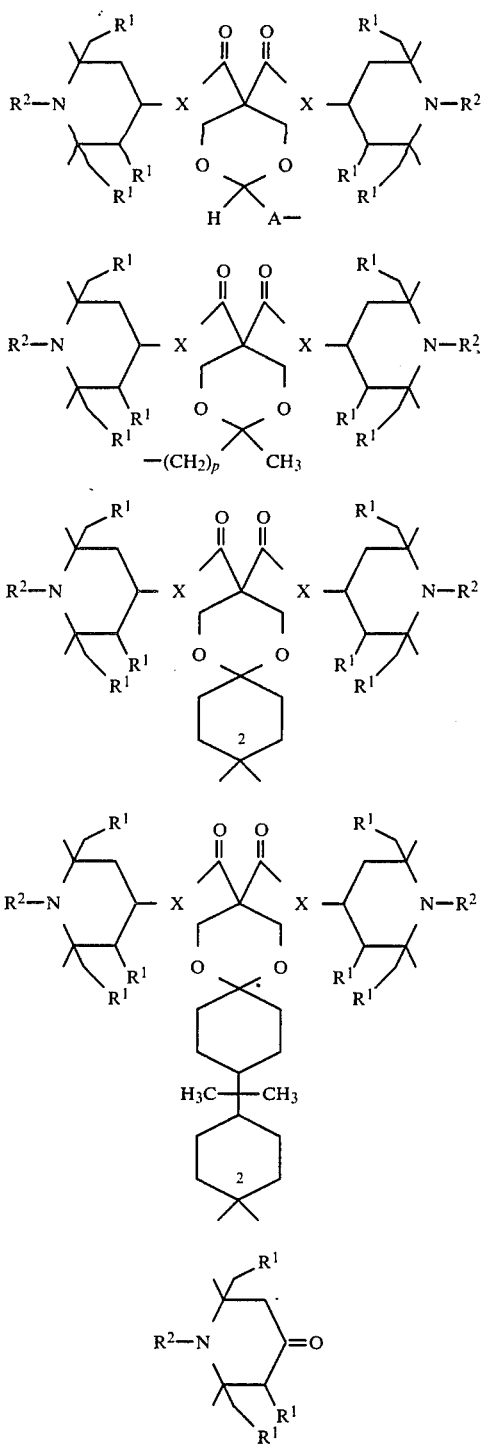

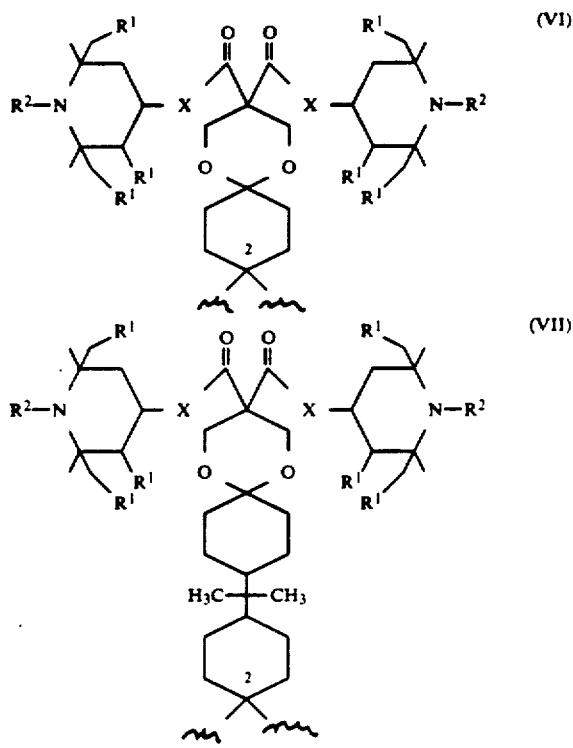

What is claimed is:
1. A compound of the formula I wherein
$R^1$ is selected from hydrogen and an alkyl group of 1-5 carbon atoms,
$R^2$ is selected from hydrogen, oxyl, hydroxyl, a straight or branched chain methylene linked alkyl group having from 1 to 18 carbon atoms, an alkanoyl group having 2-18 carbon atoms, an alkenoyl group having 3 to 6 carbon atoms, an alkynyl group having 3 to 6 carbon atoms, a cyanomethyl group, a 2,3-epoxypropyl group, a benzyl or an alkyl substituted benzyl group having 7-15 carbon atoms a group-$CH_2CH(OR^5)$—$R^6$ and a group of the formula

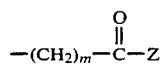

wherein Z is a group selected from -$OR^7$ and —$N(R^8)(R^9)$ when m is 1 or 0 and when m is 0, Z can be a group —CO—$OR^{10}$, wherein
$R^5$ is selected from hydrogen, a straight or branched chain methylene linked alkyl group having from 1 to 18 carbon atoms, an alkanoyl group having 2-18 carbon atoms, an alkenoyl group having 3 to 6 carbon atoms, an alkynyl group having 3 to 6 carbon atoms, a cyanomethyl group, a 2,3-expoxypropyl group, a benzyl or an alkyl substituted benzyl group having 7-15 carbon atoms,
$R^6$ is selected from hydrogen, an alkyl group of 1 to 16 carbon atoms and phenyl,
$R^7$ is selected from an alkyl group from 1 to 18 carbon atoms, a cycloalkyl group of 5-12 carbon atoms, and a group of formula II,
$R^8$ and $R^9$, same or different, are selected from hydrogen, an alkyl group having 1-18 carbon atoms, a cycloalkyl group having 5-12 carbon atoms, aryl groups having 6-10 carbon atoms and aralkyl groups having 7-15 carbon atoms, $R^8$ and $R^9$ together with the nitrogen atom to which they are attached can form a 5-7 membered ring selected from the group consisting of pyrrolidine, piperidine and homopiperidine,
$R^{10}$ is selected from an alphatic group of 1-18 carbon atoms, phenyl and benzyl,
$R^3$ and $R^4$ may independently be selected from hydrogen or an alkyl group of 1-14 carbon atoms, an alkenyl group of 2-4 carbon atoms, a group —$(CH_2)_nCO$—$OR^{11}$ where n is 0 or 1, and a group of formula III, wherein
$R^{11}$ is selected from an alkyl group having up to 18 carbon atoms or a group of formula II, when $R^3$ is hydrogen $R^4$ is a group of formula IV where A is a 1-4 carbon alkylene group, a phenylene group or a direct bond, when $R^3$ is methyl $R^4$ can be a group of formula V where p is 1 or 2, $R^3$ and $R^4$ together with the carbon atoms to which they are attached can form a cycloalkyl group having 5-12 atoms or denote a group of the formula VI or the group of formula VII wherein the C atom labelled 2 is the same as that labelled 2 in formula I,
X is either —O or —$NR^{12}$—where $R^{12}$ is selected from hydrogen or an alkyl group of 1-8 carbon atoms wherein said formulas are:

Table of Structures

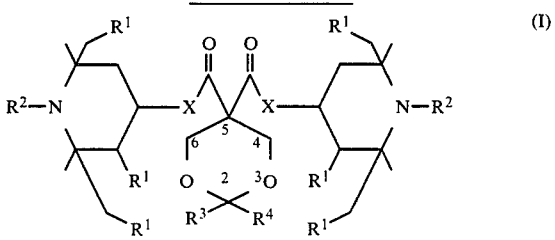

-continued
Table of Structures

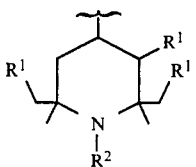
(II)

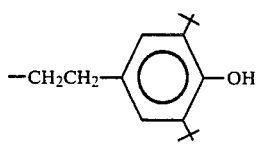
(III)

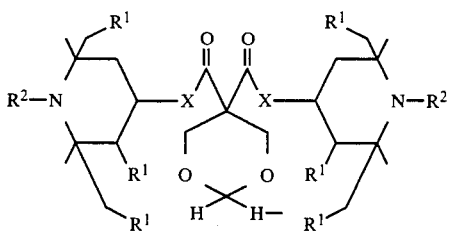
(IV)

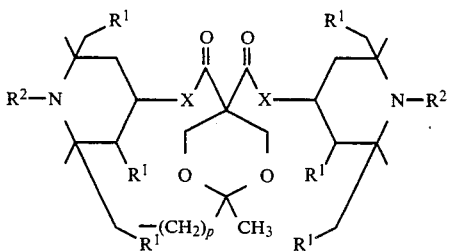
(V)

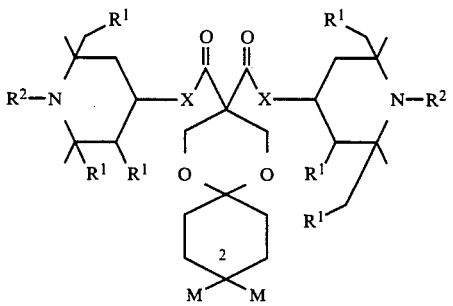
(VI)

-continued
Table of Structures

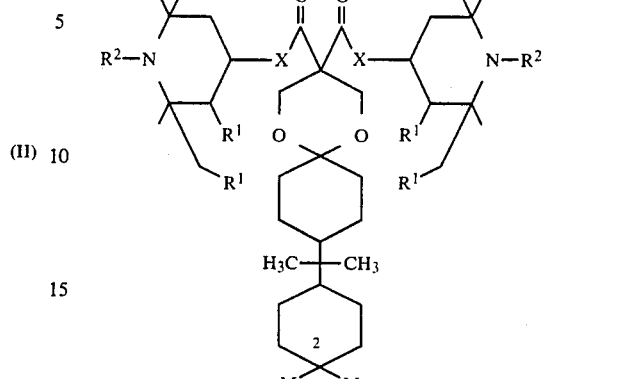
(VII)

2. A compound of claim 1 wherein $R^1$ is hydrogen, and X is —O—.

3. A compound of claim 2 which is 1,5-dioxaspiro[5.5]undecane-3,3-dicarboxylic acid, diester with 2,2,6,6-tetramethylpiperidin-4-ol.

4. A compound of claim 2 which is 1,5-dioxaspiro[5.5]undecane-3,3-dicarboxylic acid, diester with 1,2,2,6,6-pentamethylpiperidin-4-ol.

5. A compound of claim 2 which is 1,5-dioxaspiro[5.5]undecane-3,3-dicarboxylic acid, diester with 1-acetyl-2,2,6,6-tetramethylpiperidin-4-ol.

6. A compound of claim 2 which is 1,5,10,14-tetraoxadispiro[5.2.5.2]hexadecane-3,3,12,12-tetracarboxylic acid, tetraester with 2,2,6,6-tetramethylpiperidin-4-ol.

7. A compound of claim 2 which is 1, 3-bis[2,2'[1,3-dioxacyclohexane-5,5-dicarboxylic acid]]-propane, tetraester with 2,2,6,6-tetramethylpiperidin-4-ol.

8. A compound of claim 2 which is 2-[1-methylethyl]-1,3-dioxacyclohexane-5,5-dicarboxylic acid, diester with 2,2,6,6-tetramethylpiperidin-4-ol.

9. A compound of claim 2 which is 2-vinyl-1,3-dioxacyclohexane-5,5-dicarboxylic acid, diester with 2,2,6,6-tetramethylpiperidin-4-ol.

10. A compound of claim 2 which is 2-[3-heptyl]-1,3-dioxacyclohexane-5,5-dicarboxylic acid, diester with 2,2,6,6-tetramethylpiperidin-4-ol.

11. A compound of claim 2 which is 1,2-bis[2,2'[2-,methyl-1,3-dioxacyclohexane-5,5-dicarboxylic acid]]-ethane, tetraester with 2,2,6,6,-tetramethylpiperidin-4-ol.

12. A compound of claim 2, which is 2-[2-[3,5-di-tert-butyl-4-hydroxy-phenyl]]ethyl-2-methyl-1,3-dioxacyclohexane-5,5-dicarboxylic acid, diester with 2,2,6,6-tetramethylpiperidin-4-ol.

13. A compound of claim 2 which is 1,5-dioxaspiro[5.11]heptadecane-3,3-dicarboxylic acid, diester with 2,2,6,6-tetramethylpiperidin-4-ol.

14. A synthetic polymer composition stabilized against light induced deterioration comprising an organic polymer normally subject to deterioration by light, and from 0.01-5% by weight of a compound of claim 1.

15. A composition of claim 14 wherein the organic polymer is a polyolefin homopolymer or copolymer.

16. A composition of claim 15 wherein said polyolefin is polypropylene.

17. A method of stabilizing organic polymers against light induced deterioration which comprises incorporating therewith from 0.01-5% by weight of a compound of claim 1.

* * * * *

UNITED STATES PATENT AND TRADEMARK OFFICE
CERTIFICATE OF CORRECTION

PATENT NO. : 4,701,485

DATED : October 20, 1987

INVENTOR(S) : Richard V. Nelson and John F. Stephen

It is certified that error appears in the above-identified patent and that said Letters Patent is hereby corrected as shown below:

Formulas VI and VII in Examples 23-28, Table of Structures, Column 15 and Formulas VI and VII in the Table of Structures, Columns 17 and 18, in the claims, should appear as shown on the attached sheet.

Signed and Sealed this

Third Day of May, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,701,485

DATED : October 20, 1987

INVENTOR(S) : Richard V. Nelson and John F. Stephen

It is certified that error appears in the above-identified patent and that said Letters Patent is hereby corrected as shown below: